United States Patent
Vierling et al.

(10) Patent No.: US 9,636,284 B2
(45) Date of Patent: *May 2, 2017

(54) ORAL CARE COMPOSITIONS

(75) Inventors: Lauren Vierling, East Windsor, NJ (US); Dexter M. Williams, Dayton, NJ (US); Saroja Narasimhan, Monmouth Junction, NJ (US); E. Eric Engelman, Doylestown, PA (US); Joseph J. LiBrizzi, Hillsborough, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/751,096

(22) Filed: Mar. 31, 2010

(65) Prior Publication Data

US 2011/0243861 A1 Oct. 6, 2011

(51) Int. Cl.
| | | |
|---|---|---|
| *A61Q 11/00* | (2006.01) | |
| *A61K 8/04* | (2006.01) | |
| *A61K 8/44* | (2006.01) | |
| *A61K 8/60* | (2006.01) | |
| *A61K 8/73* | (2006.01) | |

(52) U.S. Cl.
CPC ............ *A61K 8/044* (2013.01); *A61K 8/44* (2013.01); *A61K 8/442* (2013.01); *A61K 8/604* (2013.01); *A61K 8/73* (2013.01); *A61Q 11/00* (2013.01); *A61K 2800/5422* (2013.01); *A61K 2800/5424* (2013.01); *A61K 2800/5428* (2013.01); *A61K 2800/592* (2013.01); *A61K 2800/596* (2013.01)

(58) Field of Classification Search
CPC .......................... A61K 2300/00; A61Q 11/00
USPC ........................................................ 424/49
See application file for complete search history.

(56) References Cited

U.S. PATENT DOCUMENTS

| | | | |
|---|---|---|---|
| 3,959,458 A | 5/1976 | Agricola | |
| 4,051,234 A | 9/1977 | Gieske | |
| 4,193,988 A * | 3/1980 | Forward et al. | 424/52 |
| 4,326,053 A | 4/1982 | Kang | |
| 4,377,636 A | 3/1983 | Kang | |
| 4,385,123 A | 5/1983 | Kang | |
| 4,503,084 A | 3/1985 | Baird | |
| 4,563,366 A | 1/1986 | Baird | |
| 5,176,899 A * | 1/1993 | Montgomery | 424/50 |
| 5,190,747 A | 3/1993 | Sekiguchi et al. | |
| 5,190,927 A | 3/1993 | Chang | |
| 5,328,682 A * | 7/1994 | Pullen et al. | 424/49 |
| 5,628,985 A * | 5/1997 | Stiller et al. | 424/49 |
| 5,780,046 A * | 7/1998 | Humber et al. | 424/440 |
| 5,833,956 A * | 11/1998 | Gorlin et al. | 424/49 |
| 5,885,556 A * | 3/1999 | Lukacovic et al. | 424/57 |
| 6,045,813 A | 4/2000 | Ferguson | |
| 6,106,815 A | 8/2000 | Kang | |
| 6,121,315 A | 9/2000 | Nair | |
| 6,602,996 B1 | 8/2003 | Sworn | |
| 6,682,722 B2 | 1/2004 | Majeti | |
| 6,797,683 B2 | 9/2004 | Shana'a | |
| 7,084,104 B2 | 8/2006 | Martin | |
| 7,087,650 B2 | 8/2006 | Lennon | |
| 7,601,338 B2 | 10/2009 | Masters | |
| 2003/0100078 A1 | 5/2003 | Harding | |
| 2003/0118522 A1* | 6/2003 | Leinen et al. | 424/54 |
| 2004/0047822 A1 | 3/2004 | Zamudo Tena | |
| 2005/0266138 A1 | 12/2005 | Yuan | |
| 2006/0093562 A1 | 5/2006 | Kellar et al. | |

FOREIGN PATENT DOCUMENTS

| | | |
|---|---|---|
| EP | 2281546 A2 | 2/2011 |
| JP | H08-333226 A | 12/1996 |
| JP | 2003-530336 A | 10/2003 |
| JP | 2004300120 A * | 10/2004 |
| JP | 2006502141 | 1/2006 |
| JP | 2009510192 | 3/2009 |
| JP | 2009084277 | 4/2009 |
| WO | WO 93/08792 | 5/1993 |
| WO | WO 9846715 | 10/1998 |
| WO | WO 99/09951 A1 | 3/1999 |

* cited by examiner

*Primary Examiner* — Frederick Krass
*Assistant Examiner* — Tracy Liu

(57) ABSTRACT

The present invention relates generally to oral care compositions, and more specifically to oral care compositions suitable for cleaning the oral cavity. Methods of use are also disclosed.

20 Claims, No Drawings

ORAL CARE COMPOSITIONS

FIELD OF THE INVENTION

The present invention relates generally to oral care compositions, and more specifically to oral care compositions suitable for cleaning the oral cavity. Methods of use are also disclosed.

BACKGROUND OF THE INVENTION

Oral hygiene compositions fall into two main categories: dentifrices, and mouthwashes or rinses. Dentifrices generally contain an insoluble dentally acceptable abrasive which is utilized to physically cleanse the surface of the teeth. Dentifrices are generally provided in the form of solid or pasty preparations which can be readily applied to a toothbrush, for example, powders, pastes or viscous gels.

Known mouthwash or mouth rinse compositions usually are solutions containing small amounts of colorings, flavorings and antibacterial or other active ingredients. These solutions have found use as breath-freshening, anti-cavity, antiseptic and/or anti-plaque mouth rinses, or gargle preparations and are commonly used in addition to conventional tooth cleansing dentifrices.

While mouth rinses and abrasive dentifrices have been produced as separate products for many years, a satisfactory form of combined product is desired in which an effective amount of abrasive is maintained in an acceptable stable suspension having a sufficiently low viscosity that the preparation can be swished between and around teeth.

There remains, therefore, a need for oral compositions, combining the benefits of both a toothpaste and a mouthwash.

SUMMARY OF THE INVENTION

In certain embodiments, the present invention relates to compositions having the following physical properties:
- a tan delta of less than 1 (or about 1) at frequencies of 0.1 to 100, optionally 0.1, rads$^{-1}$,
- a first (or pourability) viscosity of less than 2000 (or about 2000) centipoise at a shear rate of 10 s$^{-1}$, and
- a second (or swishability) viscosity of less than 1000 (or about 1000) centipoise at a shear rate of 100 s$^{-1}$.

In specific embodiments, the present invention relates to gel or liquid gel dentifrices having the following physical properties:
- a tan delta of less than 1 (or about 1) at frequencies of 0.1 to 100, optionally 0.1, rads$^{-1}$,
- a first (or pourability) viscosity of less than 2000 (or about 2000) centipoise at a shear rate of 10 s$^{-1}$, and
- a second (or swishability) viscosity of less than 1000 (or about 1000) centipoise at a shear rate of 100 s$^{-1}$.

In other embodiments, the present invention relates to swishable liquid gel dentifrice compositions which, after swishing in the mouth, provide adequate foaming even after a portion, substantial portion or the bulk of the dentifrice is expelled, swallowed or otherwise removed from the mouth, generating the foam from the coating of the composition retained on the teeth tongue or other oral surfaces of the mouth after composition is removed.

Alternatively, the present invention relates to a gel or liquid gel mouth rinse that provides a toothpaste-like sensation after a portion, substantial portion or the bulk of the gel or liquid gel mouth rinse is expelled, swallowed or otherwise removed from the mouth.

In still other embodiments, the present invention relates to liquid compositions comprising:
- a) optionally, from 0.1% (or about 0.1%) to 50% (or about 50%) by weight of a insoluble particulate such as a non-abrasive particle or dentally acceptable abrasive,
- b) optionally, from 0.01% (or about 0.01%) to 5% (or about 5%) by weight of suspending polymer,
- c) from 0.001% (or about 0.001) to about 12% (or about 12%) of a surfactant or surfactant system, and
- d) at least 45% (or about 45%) of a liquid carrier.

In an alternative embodiment, the present invention relates to oral care compositions comprising:
- a) from 0.1% (or about 0.1%) to 50% (or about 50%) by weight of a insoluble particulate such as a nonabrasive particle or dentally acceptable abrasive;
- b) from 0.01% (or about 0.01%) to 5% (or about 5%) by weight of suspending polymer;
- c) from 0.1% (or about 0.1%) to 5% (or about 5%) surfactant or surfactant system; and
- d) at least 45% (or about 45%) of a liquid carrier,
wherein said composition has a tan delta of less than 1 (or about 1) at frequencies 0.1 to 100 rads$^{-1}$ and wherein the composition is essentially free of bioavailability affecting compounds.

In other embodiments, the present invention relates to oral care compositions consisting essentially of:
- a) from 0.1% (or about 0.1%) to 50% (or about 50%) by weight of a insoluble particulate such as a nonabrasive particle or dentally acceptable abrasive;
- b) from 0.01% (or about 0.01%) to 5% (or about 5%) by weight of suspending polymer;
- c) from 0.1% (or about 0.1%) to 5% (or about 5%) surfactant; and
- d) at least 45% (or about 45%) of a liquid carrier,
wherein said composition has a tan delta of less than about 1 at frequencies 0.1 to 100 rads$^{-1}$.

In still other embodiments, the present invention relates to oral care compositions, comprising:
- a) from 0.1% (or about 0.1%) to 50% (or about 50%) by weight of a insoluble particulate such as a nonabrasive particle or dentally acceptable abrasive;
- b) from 0.01% (or about 0.01%) to 5% (or about 5%) by weight of polysaccharide gum;
- c) from 0.1% (or about 0.1%) to 5% (or about 5%) surfactant; and
- d) at least 45% (or about 45%) of a liquid carrier,
wherein said composition has a tan delta of less than 1 (or about 1) at frequencies of 0.1 to 100, optionally 0.1, rads$^{-1}$.

In further embodiments, the present invention relates to compositions, comprising:
- a. a surfactant system, comprising:
  - i. at least one nonionic surfactant;
  - ii. at least one anionic surfactant; and
  - iii. at least one amphoteric surfactant,
  and
- b. a liquid carrier,
optionally, wherein the composition has the following physical properties:
  - i. a tan delta of less than about 1 at frequencies 0.1 to 100 rads$^{-1}$;
  - ii. a first viscosity of less than about 2000 centipoise at a shear rate of 10 s$^{-1}$; and
  - iii. a second viscosity of less than about 1000 centipoise at a shear rate of 100 s$^{-1}$,
and wherein foams generated by the composition using the foam generation and screening test described below have a bubble size distribution such that for each 0.005 grams of foam having at least about 30 bubbles having a diameter of less than about 50 microns. and, or alternatively, wherein for each 0.005 grams of the foam occupying an area of 25 mm×75 mm×1.270 mm, at least 90%, optionally at least 95%, optionally at least 98% of the bubbles have a diameter of less than 50 (or about 50) microns.

In still further embodiments, the present invention relates to methods of manufacturing a composition comprising the steps of:
  a. providing a surfactant system, comprising:
    i. at least one nonionic surfactant;
    ii. at least one anionic surfactant; and
    iii. at least one amphoteric surfactant,
  and
  b. optionally, providing a suspending agent; and
  c. mixing the surfactant system and, optionally, suspending agent with a liquid carrier to produce a composition having the following physical properties:
    i. a tan delta of less than about 1 at frequencies 0.1 to 100 rads$^{-1}$;
    ii. a first viscosity of less than about 700 centipoise at a shear rate of 10 s$^{-1}$; and
    iii. a second viscosity of less than about 150 centipoise at a shear rate of 100 s$^{-1}$,
  and wherein foams generated by the composition using the foam generation and screening test described below have a bubble size distribution such that for each 0.005 grams of foam having at least about 80 bubbles having a diameter of less than about 50 microns and, or alternatively, wherein for each 0.005 grams of the foam occupying an area of 25 mm×75 mm×1.270 mm, at least 90%, optionally at least 95%, optionally at least 98% of the bubbles have a diameter of less than 50 (or about 50) microns.

In certain other embodiments, the present invention relates to compositions, comprising:
  a. at least one surfactant or a surfactant system, comprising:
    i. at least one nonionic surfactant;
    ii. at least one anionic surfactant; and
    iii. at least one amphoteric surfactant
  b. a foam enhancing agent; and
  c. a liquid carrier,
  optionally, wherein the composition has the following physical properties:
    i. a tan delta of less than about 1 at frequencies 0.1 to 100 rads$^{-1}$;
    ii. a first viscosity of less than about 700 centipoise at a shear rate of 10 s$^{-1}$; and
    iii. a second viscosity of less than about 150 centipoise at a shear rate of 100 s$^{-1}$,
  and wherein foams generated by the composition using the foam generation and screening test described below have a bubble size distribution such that for each 0.005 grams of foam having at least about 150 bubbles having a diameter of less than about 50 microns and, or alternatively, wherein for each 0.005 grams of the foam occupying an area of 25 mm×75 mm×1.270 mm, at least 90%, optionally at least 95%, optionally at least 98% of the bubbles have a diameter of less than 50 (or about 50) microns.

In still further embodiments, the present invention relates to methods of manufacturing a composition comprising the steps of:
  1. providing at least one surfactant or a surfactant system, comprising:
    a. at least one nonionic surfactant;
    b. at least one anionic surfactant; and
    c. at least one amphoteric surfactant,
  and
    d. optionally, providing a suspending agent; and
    e. mixing the surfactant system and, optionally, suspending agent with a liquid carrier to, optionally, produce a composition having the following physical properties:
      i. a tan delta of less than about 1 at frequencies 0.1 to 100 rads$^{-1}$;
      ii. a first viscosity of less than about 700 centipoise at a shear rate of 10 s$^{-1}$; and
      iii. a second viscosity of less than about 150 centipoise at a shear rate of 100 s$^{-1}$,
  wherein the composition is capable of generating a foam by using the foam generation and screening test described below where the foam has a bubble size distribution such that for each 0.005 grams of foam, at least about 80 bubbles having a diameter of less than about 50 microns and, or alternatively, wherein for each 0.005 grams of the foam occupying an area of 25 mm×75 mm×1.270 mm, at least 90%, optionally at least 95%, optionally at least 98% of the bubbles have a diameter of less than 50 (or about 50) microns.

Another embodiment of the present invention relates to a method of generating foam in the mouth comprising the steps of:
  a. providing a composition comprising:
    i. at least one surfactant or a surfactant system;
    ii. optionally, a suspending agent; and
    iii. a liquid carrier,
  wherein the composition is capable of generating a foam by using the foam generation and screening test described below where the foam has a bubble size distribution such that for each 0.005 grams of foam, at least about 80 bubbles have a diameter of less than about 50 microns and wherein for each 0.005 grams of the foam occupying an area of 25 mm×75 mm×1.270 mm, at least 90% of the bubbles have a diameter of less than about 50 microns,
  b. introducing a sufficient quantity of the composition for swishing in the mouth; and
  c. swishing the composition in the mouth to generate a foam.

Another embodiment of the present invention relates to a method of generating foam in the mouth comprising the steps of:
  a. providing a composition comprising:
    i. at least one surfactant or a surfactant system, comprising;
    ii. optionally, a suspending agent; and
    iii. a liquid carrier;
  wherein the composition is capable of generating a foam by using the foam generation and screening test described below where the foam has a bubble size distribution such that for each 0.005 grams of foam, at least about 80 bubbles have a diameter of less than about 50 microns and wherein for each 0.005 grams of the foam occupying an area of 25 mm×75 mm×1.270 mm, at least 90% of the bubbles have a diameter of less than about 50 microns.
  b. contacting the mucosal and tooth surfaces of the oral cavity with the composition; and
  c. brushing the teeth to generate a foam.

Another embodiment of the present invention relates to a composition comprising:
1. at least one surfactant or a surfactant system, and
2. optionally, at least one suspending agent
wherein the composition is capable of forming a
   a. a first liquid phase wherein, at a first moment in time, the composition has the following physical properties:
      i. a first viscosity of less than about 2000 centipoise at a shear rate of 10 s$^{-1}$; and
      ii. a second viscosity of less than about 1000 centipoise at a shear rate of 100 s$^{-1}$;
      and
   b. a second foam phase, when foamed using a foam generation and screening test, such that a bubble size distribution for each 0.005 grams of foam is at least about 80 bubbles has a diameter of less than about 50 microns and a bubble size distribution such that for each 0.005 grams of the foam occupying an area of 25 mm×75 mm×1.270 mm is at least 90% of the bubbles have a diameter of less than 50 microns.

Another embodiment of the present invention relates to a composition comprising:
1. at least one surfactant or a surfactant system, and
2. optionally, at least one suspending agent,
wherein the composition has a substantivity such that a sufficient amount remains in the oral cavity after expectoration, swallowing or otherwise removing the composition from the mouth to form a film on at least one tooth and wherein the composition is capable of forming
   a. a first liquid phase wherein, at a first moment in time, the composition has the following physical properties:
      i. a first viscosity of less than about 2000 centipoise at a shear rate of 10 s$^{-1}$; and
      ii. a second viscosity of less than about 1000 centipoise at a shear rate of 100 s$^{-1}$;
      and
   b. a second foam phase, when foamed using the foam generation and screening test described below such that a bubble size distribution for each 0.005 grams of foam is at least about 80 bubbles has a diameter of less than about 50 microns and a bubble size distribution such that for each 0.005 grams of the foam occupying an area of 25 mm×75 mm×1.270 mm is at least 90% of the bubbles have a diameter of less than 50 microns.

In addition, other embodiments of the present invention relate to methods of cleaning the oral cavity where an effective amount of the oral care compositions of the present invention are: i) introduced into the oral cavity (such as by sipping a quantity of the composition), ii) swished around the oral cavity for a sufficient amount of time to coat the teeth and mucosal surfaces of the oral cavity and iii) a portion, substantial portion or the bulk of the composition being expelled, swallowed or, otherwise removed from the oral cavity. As used herein the term "bulk of the composition" means that portion of the composition which is not retained by the hard and soft tissues of the oral cavity. Optionally, the teeth can be brushed with a toothbrush if so desired.

DETAILED DESCRIPTION OF THE INVENTION

The oral care compositions of the present invention can comprise, consist of, or consist essentially of the essential elements and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All patent documents incorporated herein by reference in their entirety are only incorporated herein to the extent that they are not inconsistent with this specification.

All percentages, parts and ratios are based upon the total weight of the composition of the present invention, unless otherwise specified. All such weights as they pertain to the listed ingredients are based on the active level and, therefore, do not include carriers or by-products that may be included in commercially available materials, unless otherwise specified.

Unless indicated otherwise, all measurements and tests described herein are conducted at a temperature of 25° C. (or about 25° C.).

The term "safe and effective amount" as used herein means an amount of a compound or composition such as a topical or system active sufficient to significantly induce a positive benefit, for example, an antimicrobial effect, but low enough to avoid serious side effects, i.e., to provide a reasonable benefit to risk ratio, within the scope of sound judgment of the skilled artisan.

As used herein the phrase "dentally acceptable" means the compound, substance or device may be administered to or into the oral cavity and/or surfaces of the oral cavity, including the teeth and gums, without substantial harmful effects to the oral cavity and/or its surfaces.

As used herein the terms "formulation" and "composition" are used interchangeably.

All viscosity measurements are obtained using an RFSII rheometer (TA Instruments, New Castle, Del.) with couette geometry.

In certain embodiments, the present invention is a liquid gel dentifrice having rheological properties such that the liquid gel dentifrice is swishable in the mouth.

The oral care compositions of the present invention, including the essential and optional components thereof, are described in detail hereinafter.

Insoluble Particulate

In certain embodiments, the oral care compositions of the present invention comprise a safe and effective amount of a water insoluble particulate. The water insoluble particulate can be an abrasive particle (such as a dentally acceptable abrasive) or non-abrasive particulate.

In certain embodiments, dentally acceptable abrasives include, but are not limited to, water insoluble calcium salts such as calcium carbonate, and various calcium phosphates, alumina, silica, synthetic resins and mixtures thereof. Suitable dentally acceptable abrasives may generally be defined as those having a radioactive dentine abrasion value (RDA) of from about 30 to about 250 at the concentrations used in the compositions of the present invention. In certain embodiments, abrasives are non-crystalline, hydrated, silica abrasives, particularly in the form of precipitated silica or milled silica gels available commercially, for example, under the trade names ZEODENT (J. M. Huber Corporation, Edison, N.J.), and SYLODENT (W.R. Grace & Co., New York, N.Y.), respectively. In certain embodiments, the compositions according to the present invention comprise from about 1% to about 20%, or, optionally, from about 5% to about 10% by weight of the abrasive.

Alternatively, the insoluble particulate is a non-abrasive particulate which is visible to the unaided eye and stable in the compositions of the present invention.

The non-abrasive particulate can be of any size, shape, or color, according to the desired characteristic of the product, so long as it is distinctively detected as an individual particle by the unaided eye. The non-abrasive particulates will typically have the shape of a small round or substantially round ball or sphere, however, platelet or rod-shaped configurations are also contemplated herein. Generally, a non-abrasive particulate has an average diameter of from about 50 µm to about 5000 µm, optionally from about 100 µm to about 3000 µm, or optionally from about 300 µm to about 1000 µm. By the terms "stable" and/or "stability", it is meant that the abrasive or non-abrasive particulates are not disintegrated, agglomerated, or separated under normal shelf conditions. In certain embodiments, the terms "stable" and/or "stability" further mean that the compositions of present invention contain no visible (to the unaided eye) signs of sedimentation of the insoluble particulates after 8 weeks, optionally 26 weeks, optionally 52 weeks, at room temperature.

The non-abrasive particulates herein are typically incorporated in the present compositions at levels of from about 0.01% to about 25%, optionally, from about 0.01% to about 5%, or optionally, from about 0.05% to about 3%, by weight of the composition.

The non-abrasive particulate herein will typically comprise a structural material and/or, optionally, an encompassed material.

The structural material provides a certain strength to the non-abrasive particulates so that they retain their distinctively detectable structure in the compositions of the present invention under normal shelf conditions. In one embodiment, the structural material further can be broken and disintegrated with very little shear on the teeth, tongue or oral mucosa upon use.

The non-abrasive particulates can be solid or liquid, filled or un-filled, as long as they are stable in the compositions of the present invention. The structural material used for making the non-abrasive particulates varies depending on the compatibility with other components, as well as material, if any, to be encompassed in the non-abrasive particulates. Exemplary materials for making the non-abrasive particulates herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), poly(ε-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. In certain embodiments, the components as described in this section form the structure of the non-abrasive particulates so as to not be substantially dissolved or dispersed from the particulates and into the compositions of the present invention under normal shelf conditions.

In other embodiments, the structural material herein comprises components selected from the group consisting of polysaccharides and their derivatives, saccharides and their derivatives, oligosaccharides, monosaccharides, and mixtures thereof, or optionally, comprises components are having various degrees of water solubility. In some embodiments, the structural material comprises lactose, cellulose, and hydroxypropyl methylcellulose.

Suitable non-abrasive particulates also include organogel particles as described in detail in U.S. Pat. No. 6,797,683. Non-abrasive particulates that are organogel particles typically comprise a structural material selected from poloxamer compounds (i.e. polyoxypropylene-polyoxyethylene block copolymer such as Pluronic F-127 available from BASF), waxes (e.g., beeswax, paraffin, water-insoluble wax, carbon-based wax, silicone wax, microcrystalline wax, etc.), triglycerides, acid triglycerides, polymers, fluoroalkyl (meth) acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted) sugars, dibenzyl sorbitol (or mannitoal, rabbitol, etc.), condensates and pre-condensates of lower monohydric alcohols, trihydroic alcohols, lower polyglycols, propylene/ethylene polycondensates, and the like. Optionally, structural material for non-abrasive particulates that are organogel particles include beeswax, carnauba wax, low molecular weight ethylene homopolymers (e.g. Polywax 500, Polywax 1000, or Polywax 2000 polyethylene materials available from Baker Petrolite Corp.), or paraffin wax.

The non-abrasive particulates herein may encompass, contain, or be filled with an encompassed material. Such encompassed material can be water soluble or water insoluble. Suitable encompassed materials include benefit agents as described herein such as: oral care actives, vitamins, pigments, dyes, antimicrobial agents, chelating agents, optical brighteners, flavors, perfumes, humectants, and mixtures thereof. The encompassed materials herein are substantially retained within the non-abrasive particulates, and are substantially not dissolved from the particulates and into the compositions of the present composition under normal shelf conditions.

Particularly useful commercially available non-abrasive particulates herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear and with practically no resistance, and readily disperse in the compositions of the present invention.

Suitable non-abrasive particulates for incorporation in the present compositions are described in detail in U.S. Pat. No. 6,797,683 (organogel particles); U.S. Pat. No. 6,045,813 (rupturable beads); U.S. 2004/0047822 A1 (visible capsules); and U.S. Pat. No. 6,106,815 (capsulated or particulated oily substances), each of which patent documents are herein incorporated by reference in their entirety.

In certain embodiments, the abrasive and/or nonabrasive particles have a density different or, optionally, substantially different from the carrier in which these particles are formulated.

Suspending Agent

In certain embodiments, the oral care compositions according to the present invention also contain at least one suspending agent suitable for maintaining solid particles (such as abrasives) in a substantially stable suspension during storage without over-thickening the composition.

In certain embodiments, the suspending agents comprise, consist essentially of or consist of organic suspending agents. In more specific embodiments, the suspending agents comprise, consist essentially of or consist of water-soluble suspending agents such as polysaccharide gums. In embodiments where the suspending agents consist essentially of or consist of organic suspending agents and/or water soluble suspending agents, the suspending agent is free of compounds which tend to or might affect the bioavailability of actives such as oral care actives incorporated in compositions with the suspending agent.

In certain embodiments, suitable suspending agents include polysaccharide gums, or optionally specific, anionic gums, such as gellan and xanthan, available commercially for example under the trade names, respectively, KELCO-GEL and KELTROL (CP Kelco U.S., Inc. Atlanta, Ga.), and mixtures thereof. In specific embodiments the xanthan gum has the following specifications:

| Particle Size | As measured using Tyler Standard Screen Scale |
| --- | --- |
| −80 mesh (180 μm) | ≥95% through |
| Loss on Drying | ≤15.0% |
| Solution pH | |
| −1% gum in deionized water | from 6.0 to 8.0 |
| Transmittance | |
| −1% gum in deionized water (600 nm) | ≥85% |
| Pyruvic Acid | ≥1.5% |
| Assay | from 91.0% to 108.0% xanthan gum |
| Ash | from 6.5% to 16.0% |
| Heavy Metals | ≤10.0 mg/kg (ppm) |
| Lead | ≤2.0 mg/kg (ppm) |
| Arsenic | ≤2.0 mg/kg (ppm) |
| Mercury | ≤1.0 mg/kg (ppm) |
| Cadmium | ≤1.0 mg/kg (ppm) |
| Isopropyl Alcohol | ≤500 mg/kg (ppm) |
| Cellulase Activity | <0.02 Absorbance Units (AU) |
| Bacteria* | |
| −48 hours | ≤100 cfu/g |
| −5 days | ≤500 cfu/g |
| Fungal (Yeast and Mold) Count | ≤100 cfu/g |
| Coliform | Negative by Most Probable Number (MPN) |
| *Escherichia coli* | Not present in 25 g |
| *Salmonella* spp. | Not present in 25 g |
| *Staphylococcus aureus* | Not present in 1.0 g |
| *Pseudomonas aeruginosa* | Not present in 1.0 g |

*Total viable mesophilic aerobic count

Xanthan gums falling within the scope of such specifications include, but are not limited to, Keltrol CG-T (CP Kelco).

In alternative embodiments, the suspending agent is gellan gum. Gellan gum(s) suitable for use herein is/are described in detail in U.S. Pat. Nos. 4,326,052 to Kang et al.; 4,326,053 to Kang et al.; 4,377,636 to Kang et al., 4,385,123 to Kang et al.; 4,377,636 to Baird et al.; 4,385,123 to Baird et al.; 4,563,366 to Baird et al.; 4,503,084 to Baird et al.; 5,190,927 to Chang. et al.; and U.S. Pat. Pub. No. 2003/0100078 to Harding et al., each of which patent documents are herein incorporated by reference in their entirety. In specific embodiments, the gellan gum is high acyl gellan gum. Suitable high acyl gellan gums are described in detail in U.S. Pat. No. 6,602,996 to Sworn et al. and U.S. Pat. Pub. No. US20050266138 to Yuan et al., both of which are herein incorporated by reference in their entirety.

Suitable suspending agents also include microcrystalline cellulose or a mixture of microcrystalline cellulose and carboxymethylcellulose sodium. Microcrystalline cellulose and mixtures of microcrystalline cellulose and carboxymethylcellulose sodium (hereinafter MCC/CMC) are available from FMC Corporation (Philadelphia, Pa.) under the trade name Avicel®. In certain embodiments, such mixtures have a ratio of microcrystalline cellulose to carboxymethylcellulose sodium of from about 20:1 to about 1:1, optionally from about 15:1 to about 3:1, or optionally, from about 10:1 to about 5:1.

In specific embodiments, microcrystalline cellulose and carboxymethylcellulose sodium is Avicel CL-611 (85% microcrystalline cellulose with 70% colloidal content, co-processed with 15% low viscosity carboxymethyl cellulose). Other useful colloidal MCC/CMCs include, but not limited to, Avicel PC-611 (85% microcrystalline cellulose with 70% colloidal content, co-processed with 15% low viscosity carboxymethyl cellulose), Avicel® RC 581 (89% microcrystalline cellulose with 70% colloidal content, co-processed with 11% medium viscosity carboxymethyl cellulose); Avicel® RC 591 (88% microcrystalline cellulose with 70% colloidal content, co-processed with 12%, 50/50 medium/low viscosity carboxymethyl cellulose); and Avicel® RC 501 (91% microcrystalline cellulose with 70% colloidal content, co-processed with 9% medium viscosity carboxymethyl cellulose). Mixtures of the above MCC/CMC mixtures may also be used.

Also useful as the suspending polymer are chemically modified clay(s). The term "chemically modified clays" as used herein means that the clays have been chemically modified either during their formation or after their formation such that the clays have no or substantially no affinity for fluoride ions and/or other oral care actives so as to reduce the bioavailability such ions or actives when used in combination. Suitable chemically modified clays include, but are not limited to, fluoride ion modified magnesium silicate clays such as Laponite DF (Rockwood Additives Limited, Cheshire, U.K.); tetrapotassium pyrophosphate/tetrasodium pyrophosphate modified magnesium aluminum silicate clays such as Veegum D (R.T. Vanderbilt, Norwalk, Conn.) and mixtures thereof.

In certain embodiments, the suspending agent is a mixture of 1) xanthan gum with 2) a microcrystalline cellulose; a MCM/CMC mixture; mixtures of the microcrystalline cellulose and MCM/CMC; or mixtures of the various MCM/CMC mixtures.

In specific embodiments, the ratio of 1) the xanthan gum to 2) the microcrystalline cellulose; MCM/CMC mixture; mixtures of the microcrystalline cellulose and MCM/CMC; or mixtures of the various MCM/CMC mixtures is from 0.5:1 (or about 0.5:1) to 25:1 (or about 25:1), optionally, from 1:1 (or about 1:1) to 20:1 (or about 20:1), optionally from 1:1 (or about 1:1) to 10:1 (or about 10:1).

In certain embodiments, the compositions of the present invention comprise from about 0.01 to about 5%, optionally from about 0.05% to about 3%, optionally from about 0.05% to about 1%, or optionally from about 0.05% to about 0.5%, by weight of the composition of a suspending agent.

Surfactant System

In certain embodiments, surfactants, which are surface active agents, are incorporated into the compositions of the present invention to aid wetting, to improve the cleansing capability of the compositions, to produce a cosmetically acceptable foam in use, to solubilize flavoring oils when present and to improve the extent and quality of foaming produced by the oral compositions of the present invention.

In some embodiments, the present invention incorporates a surfactant system to provide adequate foam generation and/or consistency. In these embodiments, the surfactant system is capable of providing adequate foam generation and/or consistency even after a portion, substantial portion or the bulk of the composition of the present invention is expectorated, swallowed or otherwise removed from the oral cavity, the form being generated from the remaining film of the composition on the teeth, tongue or other oral or mucosal surfaces of the mouth. In other embodiments, the surfactant system of the present invention comprises a combination of amphoteric, nonionic, and amphoteric surfactants.

Surfactants suitable for use in the surfactant system are those that are reasonably stable and generate appropriate foam throughout a wide pH range. In certain embodiments, the surfactant is a combination of anionic, nonionic, amphoteric surfactants. Anionic surfactants useful herein include, but are not limited to, sarcosine type surfactants or sarcosinates; taurates such as sodium methyl cocoyl taurate; alkyl sulfates such as sodium trideceth sulfate or sodium lauryl sulfate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; block copolymers such as ethylene oxide and propylene oxide copolymers e.g. Poloxamers; ethoxylated hydrogenated castor oils available commercially for example under the trade name CRODURET (Croda Inc., Edison, N.J.), and/or ethoxylated sorbitan esters such as PEG-80 sorbitan laurate or those available commercially for example under the trade name TWEEN (Croda, Edison, N.J.); fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. Nos. 7,087,650 to Lennon; 7,084,104 to Martin et al.; 5,190,747 to Sekiguchi et al.; and 4,051,234, Gieske, et al., each of which patents are herein incorporated by reference in their entirety.

In some embodiments, it may also be possible to include cationic surfactants. Suitable cationic surfactants include, but are not limited to, cetyl trimethylammonium chloride (CTAB), hexadecyltrimethylammonium bromide (HDTAB), stearyl dimethylbenzylammonium chloride, lauryl dimethylbenzylammonium chloride, cetyl dimethylethylammonium halide, cetyl dimethylbenzylammonium halide, cetyl trimethylammonium halide, dodecyl ethyldimethylammonium halide, lauryl trimethylammonium halide, coconut alkyltrimethylammonium halide, and N,N—$C_{8-20}$-dialkyldimethylammonium halide. Other suitable compounds for the cationic surfactant include bis(hydrogenated tallow alkyl) dimethylammonium chloride which is known to adsorb onto the surface with hydrophobic groups oriented away from it, 2-hydroxydodecyl-2-hydroxyethyl dimethyl ammonium chloride and N-octadecyl-N,N',N'-tris-(2-hydroxyethyl)-1,3-diaminopropane dihydrofluoride.

In specific embodiments, the surfactant system of the present invention comprises a combination of alkyl sarcosines, alkyl polyglucosides, and alkylamidopropyl betaine surfactants.

In some embodiments, the anionic surfactant is an alkyl sarcosine which typically has an alkyl group containing from 10 to 24, optionally from 12 to 20, optionally 15 to 18 carbon atoms. Salts can be readily formed by reacting the alkyl sarcosines with an appropriate base, such as sodium, potassium, ammonium hydroxide, monoethanol amine, diethanol amine or triethanol amine. Some representative examples of sodium alkyl sarcosines which can be used include sodium lauroyl sarcosinates, sodium cocoyl sarcosinates, sodium myristol sarcosinates sodium oleoyl sarcosinates sodium stearyl sarcosinates and similar sarcosinates. In specific embodiments, the oral care compositions of the present invention incorporate sodium lauroyl sarcosinate as the sarcosine surfactant. Sodium lauroyl sarcosinate is commercially available from Chattem Chemicals, Inc. as Hamposyl® L-30.

In some other embodiments, the nonionic surfactant is an alkyl polyglucosides nonionic surfactant. In specific embodiments, the present invention incorporates long chain alkyl polyglucosides. Suitable long chain alkyl polyglucosides include condensation products of (a) a long chain alcohol containing from 6 to 22, optionally from 8 to 14 carbon atoms, with (b) glucose or a glucose-containing polymer. The alkyl polyglucosides have about 1 to about 6 glucose residues per molecule of alkyl glucoside. Suitable alkyl polyglucosides include, but are not limited to, coco glucoside, decyl glucoside, and lauryl glucoside. In other specific embodiments, the oral care compositions of the present invention incorporate lauryl glucoside as the alkyl polyglucosides. Lauryl glucoside is commercially available from Cognis Corp. as Plantaren 1200 N UP.

In some embodiments, the amphoteric surfactant is an alkylamidopropyl betaine as represented by the following structural formula

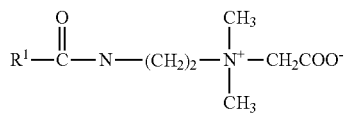

wherein $R^1$ is a long chain alkyl radical having from 1 to 18, optionally from 10 to about 16 carbon atoms. In specific embodiments, the alkylamidopropyl betaine incorporated into the oral care compositions of the present invention is cocamidopropyl betaine.

In certain embodiments, the anionic, nonionic and amphoteric surfactants are incorporated into the surfactant system at a ratio of from 80:10:10 (or about 80:10:10) to 20:40:40 (or about 20:40:40), optionally 60:20:20 (or about 60:20:20) to 40:30:30 (or about 40:30:30), or optionally 50:25:25 (or about 50:25:25).

The surfactants or surfactant systems are present at a level of from 0.001% (or about 0.001%) to 12% (or about 12%), optionally from 0.01% (or about 0.01%) to 8% (or about 8%), optionally from 0.1% (or about 0.1%) to 5% (or about 5%), or optionally from 0.2% (or about 0.2%) to 2.5% (or about 2.5%) by weight of the composition.

In some embodiments, the surfactant systems or surfactant(s) are incorporated into the compositions of the present invention and screened using a specific foam generation and screening test.

Foam Generation and Screening Test

The foam generation and screening test used to characterize the foams of the present invention comprises the steps of diluting a composition comprising the surfactant systems or surfactant(s) of the present invention with an artificial saliva solution comprising:

| | |
|---|---:|
| Sodium Chloride | 1.2236 gm |
| Potassium Chloride | 1.215 gm |
| Calcium Chloride | 0.3178 gm |
| Potassium Phosphate Monobasic | 2.7532 gm |
| Potassium Phosphate Dibasic | 3.5053 gm |
| Deionized Water | 2000 ml | such that the mixture comprises 80% of the surfactant containing composition and 20% of the artificial saliva solution, the mixture is then blended for 10 seconds using a Oster 14-speed blender (model number 6855) on the easy clean speed setting (speed setting No. 1).

A 0.005 gram sample of the foam from the surface of the mixture inside the blender was removed using a spatula.

The 0.005 gram foam sample was placed on a 25 mm×75 mm glass slide having two 0.634 mm PET spacers positioned on each corner of the slide. A second slide was placed onto the first slide and spaced by the PET spacers ensuring that there was a monolayer of foam between the two slides.

The slide was mounted on the Olympus optical microscope (model BX-51 with Discover Details 5 Image Analysis software stage), adjusting the microscope to reflectance mode and capturing the image using the 5× objective and then analyzed.

Foams generated from compositions incorporating the surfactant(s) or surfactant systems of the present invention and using the foam generation and screening test described herein have a bubble size distribution such that for each 0.005 grams of foam, at least 30 (or about 30), optionally 50 (or about 50), optionally 65 (or about 65), optionally 80 (or about 80), optionally 100 (or about 100), optionally 125 (or about 125), optionally 150 (or about 150), optionally 175 (or about 175), or optionally 200 (or about 200) bubbles have a diameter of less than 50 (or about 50) microns and additionally, or alternatively, wherein the foams have a bubble size distribution such that for each 0.005 grams of foam occupying an area of 25 mm×75 mm×1.270 mm, at least 90%, optionally at least 95%, optionally at least 98% of the bubbles have a diameter of less than 50 (or about 50) microns.

In alternative embodiments, the above mentioned surfactants are incorporated singly or in various other combinations.

Foam Enhancing Agents

In certain embodiments, the composition of the present invention incorporates a foam enhancing agent to further increase the number or percentage of bubbles having a diameter of less than 50 (or about 50) microns in the bubble size distribution generated by the surfactants or surfactant systems of the present invention.

Suitable foam enhancing agents include, but are not limited to, natural seaweed extract, natural seed gum, natural plant exudates, natural plant extracts, natural fiber extracts, biosynthetic gums, gelatins, biosynthetic process starch or cellulosic materials, alginates, carrageenans, guar, locust, tara, arabic gum, ghatti gum, agar gum, pectin, other like hydrocolloid source material, salts thereof, or mixtures thereof. Suspending agents mentioned above may also be useful as foam enhancing agents. In specific embodiments, the foam enhancing agent is selected from the group consisting of alginates, carrageenans, salts thereof or mixtures thereof. In certain other embodiments, the foam enhancing agent is carrageenan.

The foam enhancing agent(s) are present at a level of from about 0.001% to about 12%, optionally from about 0.01% to about 8%, optionally from about 0.1% to about 5%, or optionally from about 0.2 to about 2.5% by weight of the oral care composition.

In some embodiments, when the foam enhancing agents are incorporated into the compositions of the present invention with the above-mentioned surfactant systems or surfactant(s) and screened using the foam generation and screening test, the foams generated by the screening test have a bubble size distribution such that for each 0.005 grams of foam at least 150 (or about 150), optionally 200 (or about 200), optionally 225 (or about 225), optionally 250 (or about 250), optionally 275 (or about 275), optionally 300 (or about 300), optionally 325 (or about 325), optionally 350 (or about 350), optionally 375 (or about 375)), or optionally 400 (or about 400) bubbles have a diameter of less than 50 (or about 50) microns and additionally, or alternatively, wherein the foams generated by the screening test have a bubble size distribution such that for each 0.005 grams of foam occupying an area of 25 mm×75 mm×1.270 mm, at least 90%, optionally at least 95%, optionally at least 98% of the bubbles have a diameter of less than 50 (or about 50) microns.

Gas Generating Agents or Materials

In certain embodiments, gas is used to generate foam in the oral cavity. This is specifically useful in embodiments in which the teeth are manually cleaned with a clean instrument, such as a toothbrush, after a portion, substantial portion or the bulk of the composition has been removed (expectorated) from the oral cavity.

Foamable embodiments may include gas-generating materials such as, but limited to, peroxide generating compounds; alkali metal bicarbonate salts such as sodium or potassium bicarbonate in combination with organic acids; compressed air, butane, isopentane, nitrous oxide or carbon dioxide; volatile hydrocarbons or mixture of volatile hydrocarbons (of typically 3 to 6 carbons in chain length); and mixtures thereof.

Suitable peroxide generating compounds include, but not limited to, peroxides such as hydrogen peroxide, urea peroxide, calcium peroxide and mixtures thereof; perborates such as sodium perborate, potassium perborate and mixtures thereof; percarbonates such as sodium percarbonate, potassium percarbonate and mixtures thereof; metal chlorites such as calcium chlorite, barium chlorite, magnesium chlorite, lithium chlorite or sodium chlorite, potassium chlorite and mixtures thereof; peroxyacids such as peroxyacetic acid; and mixtures thereof.

In some embodiments gas can be generated by mixing two or more separated formulations prior (or just prior) to usage such as by combining acids such as tartaric acid, citric acid, fumaric acid, adipic acid, malic acid, oxalic acid, or sulfamic acid and mixtures thereof with carbonate salts such as sodium carbonate, calcium carbonate, magnesium carbonate, ammonium carbonate, potassium carbonate, sodium bicarbonate, calcium bicarbonate and mixtures thereof to produce an effervescent reaction.

In yet another embodiment gas can be generated in-vivo during usage by incorporating gaseous liquids such as carbonated liquids into the product during manufacture and/or just prior to usage. In this embodiment the invention can either be a single formulation or two or more formulations kept separated from each other and mixed prior (or just prior) to usage.

In still other embodiments, the compositions of the present invention are free of or essentially free of gas-generating agents or materials. "Essentially free" as used with respect to gas-generating agents or materials is defined as formulations having less than 5% (or about 5%), optionally, 3% (or about 3%), optionally, 1% (or about 1%), optionally, 0.01% (or about 0.01%) or zero percent, by weight of the total composition of a gas-generating agent or material.

Rheological Properties

In some embodiments, the oral care compositions or formulations are stable and pourable for rinsing, having rheological properties including the ability to suspend particles, pour easily, and be swishable in the mouth without negative viscosity build. These formulations also provide adequate substantivity such that the formulation material is retained in mouth, post expectoration (or removal), so that, if toothbrushed, the brushing experience meets consumer expectations (i.e., adequate foaming, body, mouthfeel etc.) for improving the post rinse and/or brush-sensory experience.

Dynamic mechanical rheological properties as a function of frequency and temperature are useful tools for predicting the overall physical stability of concentrated colloidal dispersions containing particulates.

By using dynamic rheology, the prediction of physical stability can often be accomplished in less than three (3) hours. The dynamic or oscillatory rheology technique is performed in two parts. First, a strain sweep test (frequency constant, strain variable) defines the linear viscoelastic range (LVR). Second, frequency scans (from 0.01 to 5.0 Hz) are performed at various temperatures, from 5 to 49° C. (40-120° F.). In certain embodiments, the frequency scans are performed in the LVR. Dynamic rheology measurements yield data on the elastic (G') and viscous (G") moduli. Plotting the elastic to viscous moduli ratio as a function of frequency and temperature generates a plot which is a "fingerprint" of the dispersion's colloidal stability. The G'/G" ratios correlate well with observed physical stability properties. Then Tan (delta) is calculated by the ratio of G" to G', or tan (delta)=G"/G'. This represents the viscous fraction to elastic fraction of the suspension.

In certain embodiments, the oral care compositions of the present invention have a Tan delta of less than 1 (or about 1), optionally less than 0.75 (or about 0.75), optionally less than 0.5 (or about 0.5), at frequencies of between 0.1 to 100 rads$^{-1}$ as measured by an RFSII rheometer (TA Instruments, New Castle, Del.) with couette geometry.

"Pourability" of oral care formulations is defined as the capability of moving in a continuous flow. The terms "Swishing" "Swishable" or "Swishability of" as they relate to the oral care compositions of the present invention mean moving or the ability to move the composition with sufficient force to produce a sibilant, or hissing, sound by movement i) through and/or around the teeth and/or ii) around the oral cavity, where such movement can occur for a period of time without noticeable tiring or fatiguing of the jaw muscles of the user.

Steady state viscosity measurements give information on relevant ranges of viscosities that may provide consumer acceptable pourability and swishability in the mouth. In certain embodiments, the compositions of the present invention have a pourability viscosity of less than 2000 (or about 2000) centipoise, optionally less than 1500 (or about 1500) centipoise, optionally less than 1000 (or about 1000), optionally less than 700 (or about 700), optionally less than 500 (or about 500) centipoise, optionally less than 300 (or about 300) centipoise, at a shear rate of 10 s$^{-1}$. In certain embodiments, the compositions of the present invention have a swishability viscosity of less than 1000 (or about 1000) centipoise, optionally less than 500 (or about 500) centipoise, optionally less than 300 (or about 300), optionally less than 150 (or about 150), optionally less than 100 (or about 100) centipoise, optionally less than 50 (or about 50) centipoise at a shear rate of 100 s$^{-1}$.

In certain embodiments, the compositions of the present invention are shear thinning Shear thinning is an effect where viscosity decreases with increasing rate of shear stress. Materials that exhibit shear thinning are called pseudoplastic.

In certain embodiments of the present invention, the oral care compositions as herein described are used regularly, from 1 to 4, optionally from 2 to 3, times daily, in place of a conventional dentifrice. A typical usage involves introducing a safe and effective amount or quantity (for example, at least 1 [or about 1], optionally, at least 5 [or about 5], optionally, at least 10 [or about 10], optionally, at least 15 [or about 15], optionally, at least 20 [or about 20] milliliters) of the oral care composition into the oral cavity, swishing the composition around the oral cavity and/or through the teeth for sufficient time to coat the teeth, and expelling, swallowing or otherwise removing a portion or substantial portion of the composition from the mouth. The composition is swished around the oral cavity and/or through the teeth for at least 10 (or about 10), optionally, at least 20 (or about 20), optionally, at least 30 (or about 30), optionally, at least 50 (or about 50), optionally, at least 75 (or about 75), optionally, at least 100 (or about 100), optionally, at least 120 (or about 120), times or swishing cycles within a period of at least 1 (or about 1), optionally, at least 5 (or about 5), optionally, at least 10 (or about 10), optionally, at least 15 (or about 15), optionally, at least 20 (or about 20), optionally, at least 30 (or about 30), optionally, at least 45 (or about 45), optionally, at least 60 (or about 60), optionally, at least 90 (or about 90) seconds.

Optionally, the teeth are brushed with a tooth cleaning instrument such as a toothbrush for a sufficient amount of time to provide desired cleaning In certain embodiments, it has been found that, upon introduction and removal of a portion, substantial portion or the bulk of the compositions of the present invention from the oral cavity, sufficient composition remains on the teeth, tongue and/or oral tissues or mucosa of the mouth to give a satisfactory foaming and abrasive action, when optionally used in conjunction with a toothbrush, and to provide a long-lasting fresh mouth feel after use.

Optional Ingredients
Oral Care Actives

In certain embodiments, the compositions of the present invention further contain oral care actives. In certain embodiments, the oral care actives include, but are not limited to, anti-plaque agents, fluoride ion sources such as sodium fluoride, sodium monofluorophosphate and amine fluorides (providing, for example, about 1-1500 ppm of fluoride ion, optionally about 200-1150 ppm of fluoride ion); anti-calculus agents such as water-soluble pyrophosphate salts, optionally, specific alkali metal pyrophosphates; chelating agents; tooth desensitization agents which reduce tooth sensitivity including potassium salts such as potassium oxalate, potassium nitrate and potassium chloride (for example about 1% to about 5% by weight) and strontium salts such as strontium chloride and strontium acetate (for example about 2% to about 10% by weight); tooth whitening agents and vitamins such as vitamin A.

In certain embodiments, suitable anti-plaque and/or anti-gingivitis agents include, but are not limited to, oral care enzymes, non-ionic antibacterial agents such as bromochlorophene and triclosan and cationic agents such as cetylpyridinium chloride and chlorhexidine salts, and mixtures thereof. Furthermore, it is known that certain water-insoluble flavoring oils such as anethole, eucalyptol, methyl salicylate, thymol and menthol have an antibacterial effect at high concentrations. In certain embodiments, the oral care compositions of the present invention comprise from about 0.001% to about 1%, optionally from about 0.01% to about 0.5% by weight of a non-ionic antibacterial agent. In some embodiments, the water-insoluble anti-tartar agents comprise zinc salts such as zinc citrate. In certain embodiments, the compositions of the present invention can comprise from about 0.1% to about 1% of a water-insoluble anti-calculus agent.

A more detailed discussion oral care actives useful in the compositions of the present invention can be found in U.S. Pat. No. 7,601,338 to Masters et al., U.S. Pat. No. 6,682,722 to Majeti et al. and U.S. Pat. No. 6,121,315 to Nair et al., both of which are herein incorporated by reference in their entirety.

Carriers and Carrier Ingredients

In certain embodiments, the compositions according to the present invention may comprise at least about 45%, optionally, at least about 60%, optionally, at least about 80% to about 99%, or, optionally, at least about 80% to about 90% by weight of a liquid carrier, but it will be understood by those skilled in the art that this proportion depends to a large extent on the proportion of abrasive incorporated into the composition. In certain embodiments, the liquid carrier may be in the form of a solution, emulsion or microemulsion of components and, in some embodiments, contain at least about 5% by weight water, optionally, at least about 10% by weight water. In certain embodiments, alcohol such as ethanol may optionally form part of the liquid carrier, for example, from about 5% to about 35% by weight of the liquid carrier, and, in some embodiments, is particularly useful in oral care compositions having a high flavor impact and breath-freshening and/or antiseptic properties. Optionally, the liquid carrier of the present invention is an orally acceptable liquid carrier. The phrase "orally acceptable" means that the carrier is suitable for application to the surfaces of the oral cavity or ingestion by a living organism including, but not limited to, mammals and humans without undue toxicity, incompatibility, instability, allergic response, and the like.

In specific embodiments, the compositions of the present invention can be in the form of mouthrinses, mouthwashes, gels, liquid gels, liquid dentifrices and the like.

In certain embodiments, the liquid carrier contains humectants, substances that promote retention of moisture, to enhance the mouthfeel of the product and to prevent drying out. In some embodiments, humectants include, but are not limited to, glycerin, sorbitol and glycols such as propylene glycol and polyethylene glycol, and mixtures thereof. In other embodiments, alternatively or in addition to the humectant, the liquid carrier may contain silicone oils, for example, in an amount of from about 0.1% to about 5% by weight. In certain clear product embodiments, where the refractive index is an important consideration, the refractive index of abrasive system can be chosen or made to match the refractive index of the carrier or solvent system.

In certain embodiments, the oral care compositions of the present invention may contain flavoring agents commonly in the form of oils commercially available as mouthwash, mouth rinse, and toothpaste flavors. In some embodiments, flavoring agents include, but are not limited to, peppermint, spearmint, aniseed, menthol, eucalyptus, clove, thymol and wintergreen, and mixtures thereof. In certain embodiments, high levels of flavoring oils can be incorporated into the oral care compositions of the present invention by forming an emulsion in the liquid carrier. This is particularly advantageous in certain embodiments, where the compositions are required to have little or no alcohol content but which need to have a high flavor impact. Conventional oral care compositions containing high flavoring concentrations generally utilize substantial levels of alcohol to dissolve the flavoring oils. In certain embodiments of the present invention, high flavoring content may also be desirable where oral care compositions contain an unpleasant tasting active ingredient, for example an agent to reduce tooth sensitivity such as strontium chloride, potassium nitrate and/or potassium oxalate or an anti-tartar agent such as tetrapotassium pyrophosphate salts. In certain embodiments, the oral care compositions according to the invention contain from about 0.01% to about 1.5%, optionally, from about 0.1% to about 1% by weight of the flavoring agent.

In certain embodiments, the oral care compositions of the invention incorporate colorings, which may be soluble coloring agents conventionally used in mouthwashes or dentifrices or may be the insoluble particulates such as color pigments or whitening agents such as titanium dioxide, pearlizing agents such as mica, or mixtures thereof. Color pigments are generally available in a wider range of colors and are less susceptible to fading than soluble coloring agents and may therefore be used to advantage in the compositions of the present invention.

In certain embodiments, the pH of the oral care compositions according to the present invention is generally in the range of from about 3.5 to about 10.0, or optionally, from about 4.0 to 8.0. In other embodiments, if desired, the pH can be controlled with acid, for example citric acid, or base, for example sodium hydroxide, or buffered, for example with citrate, phosphate, benzoate or bicarbonate buffering salts.

Various other materials may optionally be incorporated into certain embodiments of the compositions of the present invention which will be well known to those skilled in the art. These include, for example, at least one of sweeteners such as saccharin and aspartame; preservatives such as sodium benzoate and parabens. In certain embodiments, these optional additives may together comprise from about 0.01% to about 10%, optionally, from about 0.1% to about 5% by weight of the composition.

In certain embodiments, the compositions of the present invention are free of or essentially free of bioavailability affecting compounds. As used herein, "bioavailability affecting compound", means compounds that negatively affect the bioavailability of any incorporated oral care actives such as by binding the oral care actives or inactivating the oral care actives. "Essentially free" as used with respect to bioavailability affecting compounds is defined as formulations having less than 5% (or about 5%), optionally, 3% (or about 3%), optionally, 1% (or about 1%), or optionally, 0.01% (or about 0.01%), by weight of the total composition of a bioavailability affecting compound. In certain embodiments, the bioavailability affecting compound can include, but is not limited to, chemically unmodified clays, water soluble calcium salts, water soluble magnesium salts, water soluble aluminum salts, carbonate salts and mixtures thereof. In other embodiments, the oral care compositions of the present invention are free of or essentially free of chemically unmodified clays.

In certain embodiments, the compositions according to the invention may be shaken prior to use or, alternatively, provide stable suspensions during use without being shaken prior to use.

In other embodiments, the compositions according to the present invention are pourable, pleasant tasting suspensions which remain physically stable after storage, or in still further embodiments, after long-term storage, for example, for over 3 months at ambient temperatures and in particular have suitable sedimentation times, for example, greater than 3 (or about 3), 6 (or about 6), 12 (or about 12), or 24 (or about 24) months.

In certain embodiments, a further advantage of the oral care compositions according to the present invention relates to their ease of manufacture compared to the manufacture of conventional dentifrices such as toothpastes. It is well known in the art that stringent production methods are required to obtain a satisfactory toothpaste product, for example manufacture must be carried out under vacuum to prevent the formation of air bubbles which produce a visually unacceptable product and may lead to oxidation of the flavorings and syneresis (the process by which a liquid is separated from a gel owing to further coagulation) of the product. In contrast, certain embodiments of the oral care compositions of the present invention are easily formulated by dispersing the abrasive into a mixture of surfactant, suspending agent and liquid carrier, under normal production conditions without the need for an external vacuum or vacuumed environment.

The oral care compositions according to the invention are illustrated by the following examples.

EXAMPLES

The oral compositions of the present invention as described in following examples illustrate specific embodiments of compositions of the present invention, but are not intended to be limiting thereof. Other modifications can be undertaken by the skilled artisan without departing from the spirit and scope of this invention.

Example 1

Oral Care Formulations and Preparation.

A series of liquid gel dentifrices, listed in Tables 1 through 6 below, were formulated.

TABLE 1

Liquid Gel Dentifrices

| Ingredient | 1-1 w/w % | 1-2 w/w % | 1-3 w/w % |
|---|---|---|---|
| Deionized Water | 55.2806 | 55.2106 | 55.2406 |
| Citric acid | 0.0100 | 0.1000 | 0.1000 |
| Sorbitol | 20.0000 | 20.0000 | 20.0000 |
| Sodium Saccharin | 0.1170 | 0.1170 | 0.1170 |
| High acyl gellan gum | 0.1000 | 0.0500 | 0.0500 |
| Xanthan gum | — | 0.0300 | — |
| Hydrated silica | 5.0000 | 5.0000 | 5.0000 |
| Ethyl alcohol | 18.3030 | 18.3030 | 18.3030 |
| Menthol | 0.0323 | 0.0323 | 0.0323 |
| Thymol | 0.0639 | 0.0639 | 0.0639 |
| Methyl salicylate | 0.0660 | 0.0660 | 0.0660 |
| Eucalyptol | 0.0922 | 0.0922 | 0.0922 |
| Flavor | 0.0850 | 0.0850 | 0.0850 |
| Polaxamer 407 | 0.2500 | 0.2500 | 0.2500 |
| Sodium lauryl sulfate | 0.6000 | 0.6000 | 0.6000 |
| TOTAL | 100.0000 | 100.0000 | 100.0000 |

The liquid gel dentifrices of Table 1 were prepared according to the following steps. In Step A, using a first suitable beaker (herein after referring to it as the main beaker), a quantity of deionized water was added to the main beaker, the citric acid was sprinkled in and mixed until it dissolved. A Silverson L4RT high shear mixer (Silverson Machines Inc., East Longmeadow, Mass.) was used to disperse the gums. Once the gums were dispersed, the mixture was switched to Caframo mixer (Caframo Limited, Wiarton, Ontario, Canada), and stirring continued while the mixture was heated to about 85° C. The batch was held at about 85° C. for about 5 minutes. The mixture was cooled and sorbitol and saccharin were added at about 50° C. and mixed until homogeneous. Hydrated silica was added and the batch was mixed until the batch was homogeneous, and cooled to about 30° C. before the addition of the alcohol phase (from Step B).

In Step B (the alcohol phase), in a second suitable beaker, ethanol, thymol, menthol, methyl salicylate, eucalyptol, mint flavor and poloxamer 407 were combined, and mixed until homogeneous.

In Step C (the surfactant blend), in a third suitable beaker, deionized water and sodium lauryl sulfate were combined, and mixed until visually clear to unaided eye.

In the final step, the contents of the second beaker (from Step B) were added to the main beaker (of Step A) and mixed until homogenous. Finally, the contents of the third beaker (of Step C) were added to the main beaker and mixed until the batch was homogeneous.

TABLE 2

Liquid Gel Dentifrices

| Ingredient | Formulation 2-1 w/w % | 2-2 w/w % |
|---|---|---|
| Deionized Water | 55.2906 | 55.5706 |
| Citric acid | 0.1000 | 0.01000 |
| Sorbitol solution | 20.0000 | 20.0000 |
| Sodium Saccharin | 0.1170 | 0.1170 |
| Silica | 5.0000 | 4.0000 |
| Keltrol CG-T Xanthan gum | 0.3000 | — |
| P TIC Xanthan gum | — | 0.3000 |
| Ethyl alcohol | 18.3030 | 18.3030 |
| Menthol | 0.0323 | 0.0323 |
| Thymol | 0.0639 | 0.0639 |
| Methyl salicylate | 0.0660 | 0.0660 |
| Eucalyptol | 0.0922 | 0.0922 |
| Mint Flavor | 0.0850 | 0.0850 |
| FD&C Green | — | 0.0100 |
| N-Propanol | — | 0.5000 |
| Polaxamer 407 | 0.2500 | 0.2500 |
| Sodium lauryl sulfate | 0.3000 | 0.6000 |
| TOTAL | 100.0000 | 100.0000 |

The liquid gel dentifrices of Table 2 were prepared according to the following steps. In Step A, using a first suitable beaker (herein after referring to it as the main beaker), a quantity of deionized water was added to the main beaker, sprinkle in the citric acid and mixed until it dissolved. A Silverson L4RT high shear mixer (Silverson Machines Inc. East Longmeadow, Mass.) was used to disperse the gums by sprinkling them in slowly, and mixed for 5 to 10 minutes. Once gums were dispersed, the mixer was switched to a Caframo mixer (Caframo Limited Wiarton, Ontario, Canada), and mixing continued. Sorbitol and saccharin sodium were added, and the solution was mixed well until homogeneous. Then, the silica was added and mixed well until it was uniformly distributed.

In Step B (the alcohol phase), in a second suitable beaker, ethanol, n-propanol, thymol, menthol, methyl salicylate, eucalyptol, mint flavor and Poloxamer 407 were combined, and mixed well until homogeneous.

In Step C (the surfactant blend), in a third suitable beaker, deionized water and sodium lauryl sulfate, were combined and mixed until the mixture was visually clear to the unaided eye.

In the final step, the contents of the second beaker (from Step B) were added to the main beaker (of Step A) and mixed well until homogeneous. Finally, the contents of the third beaker (of Step C) were added to the main beaker and mixed until the batch was homogeneous.

TABLE 3

Liquid Gel Dentifrices

| Ingredient | Formulation 3-1 w/w % | 3-2 w/w % |
|---|---|---|
| Deionized Water | 52.3541 | 48.7400 |
| Disodium EDTA | 0.3000 | 0.3000 |
| Sodium Fluoride | 0.1878 | 0.1878 |
| Avicel CL-611 microcrystalline cellulose/ carboxy methylcellulose sodium | 1.0000 | 0.7000 |
| 1% Solution Keltrol CG-T Xanthan gum | 10.0000 | 15.0000 |
| Carrageenan | 0.0500 | 0.0500 |
| Sorbitol solution | 20.0000 | 20.0000 |
| Sucralose solution | 0.1200 | 0.1200 |
| Sodium Saccharin | 0.1170 | 0.1170 |
| Silica | 5.0000 | 5.0000 |
| Sodium Lauroyl Sarcosinate | 0.8000 | 0.8000 |
| Lauryl glucoside | 0.8000 | 0.8000 |
| Cocamidopropyl betaine | 0.4000 | 0.4000 |
| Ethyl alcohol | 8.4211 | 6.5264 |
| Polaxamer 407 | — | 0.2500 |
| Menthol | — | 0.0646 |
| Thymol | — | 0.1278 |
| Methyl salicylate | — | 0.1320 |
| Eucalyptol | — | 0.1844 |
| Mint Flavor | 0.4500 | 0.5000 |
| TOTAL | 100.0000 | 100.0000 |

The liquid gel dentifrice of Table 3 were prepared according to the following steps. In Step A, the disodium EDTA, sodium fluoride, cocamidopropyl betaine, sodium lauroyl sarcosinate, and deionized water were mixed in a first beaker until all solids were dissolved.

In Step B, xanthan gum, in the form of a powder, was added to deionized water in a second beaker to create a 1% solution. Mixing was performed in a Silverson L4RT high shear mixer (Silverson Machines Inc. East Longmeadow, Mass.) until all solids were dissolved.

In Step C, the deionized water was added to a third beaker. Using the Silverson L4RT high shear mixer, the carrageenan was dispersed in the water by sprinkling it in slowly, and mixing until homogeneous. The Avicel CL-611 microcrystalline cellulose/sodium carboxy methylcellulose was sprinkled in, and the Silverson L4RT high shear mixer continued to operate until the mixture was homogeneous. The mixer was switched to Caframo mixer (Caframo Limited Wiarton, Ontario, Canada) and mixing continued. sorbitol, sodium saccharin, and sucralose were added, and the solution was mixed well until homogeneous. The lauryl glucoside was melted, and added to the batch, and mixing was continued until homogeneous. The xanthan gum solution (Step B, second beaker) was added to the batch, and mixing continued until homogenous. Then, the silica was added and mixed until the batch was homogeneous.

In Step D (the alcohol phase), in a fourth beaker, ethanol and mint flavor, or ethanol, mint flavor, thymol, menthol, methyl salicylate, eucalyptol, and Poloxamer 407 were combined, and mixed until homogeneous.

In the final step, the contents of the fourth beaker (from Step D) were added to the third beaker (of Step C) and mixed well until homogenous. Finally, the contents of the first beaker (of Step A) were added to the main beaker and mixed until the batch was homogeneous.

TABLE 4

Liquid Gel Dentifrices

| Ingredient | Formulation 4-1 w/w % |
|---|---|
| Deionized Water | 75.1995 |
| Sodium Saccharin | 0.1000 |
| Sodium Fluoride | 0.0500 |
| Glycerine | 10.0000 |
| Methylparaben | 0.2000 |
| Montmorillonite clay | 3.5000 |
| Silica | 10.0000 |
| Sodium Lauryl Sulfate | 0.5000 |
| Dye | 0.0005 |
| Mint Flavor | 0.4500 |
| TOTAL | 100.0000 |

The liquid gel dentifrices of Table 4 were prepared according to the following steps. In Step A, the sodium saccharin, sodium fluoride, and deionized water were mixed in a first beaker until all solids were dissolved.

In Step B, the glycerine was added to a second beaker, and mixing started. Methylparaben was added, and the solution was mixed until homogeneous. Then the montmorillonite clay was added to the batch, and mixing continued until homogeneous. The contents of the first beaker (Step A) were added to the batch of second beaker, and mixing continued until homogeneous. Then, the silica was added to the second beaker and mixed until the batch was homogeneous. Finally, the sodium lauryl sulfate, flavor, and dye were sequentially added to the second beaker and mixed until the batch was homogeneous.

TABLE 5

Liquid Gel Dentifrices

| Ingredient | Formulation 5-1 w/w % |
|---|---|
| Deionized Water | 62.0366 |
| Disodium EDTA | 0.3000 |
| Sodium Fluoride | 0.0500 |
| Acryate copolymer | 3.3500 |
| Carrageenan | 0.0500 |
| Sorbitol solution | 20.0000 |
| Sucralose solution | 0.1200 |
| Sodium Saccharin | 0.1170 |
| Silica | 5.0000 |
| Sodium Lauroyl Sarcosinate | 0.8000 |
| Lauryl glucoside | 0.8000 |
| Cocamidopropyl betaine | 0.4000 |
| Ethyl alcohol | 6.5264 |
| Mint Flavor | 0.4500 |
| TOTAL | 100.0000 |

The liquid gel dentifrices of Table 5 were prepared according to the following steps. In Step A, the disodium EDTA, sodium fluoride, cocamidopropyl betaine, sodium lauroyl sarcosinate, and deionized water were mixed in a first beaker until all solids were dissolved.

In Step B, deionized water was added to a second beaker. Using a Silverson L4RT high shear mixer (Silverson Machines Inc. East Longmeadow, Mass.), the carrageenan was dispersed in the water by sprinkling them in slowly, and mixing until homogeneous. The mixer was switched to Caframo mixer (Caframo Limited Wiarton, Ontario, Canada) and mixing continued. The acryate copolymer was added, and the solution was mixed until homogeneous. Sorbitol, sodium saccharin, and sucralose were added, and the solution was mixed until homogenous. The lauryl glucoside was melted, and added to the batch, and mixing was continued until homogeneous. Then, the silica was added to the second beaker and mixed until the batch was homogeneous.

In Step C (the alcohol phase), in a third beaker, ethanol and mint flavor were combined, and mixed until homogeneous.

In the final step, the contents of the third beaker (from Step C) were added to the second beaker (of Step B) and mixed until homogenous. Finally, the contents of the first beaker (of Step A) were added to the second beaker and mixed until the batch was homogeneous.

TABLE 6

Liquid Gel Dentifrices

| Ingredient | Formulation 6-1 w/w % |
|---|---|
| Deionized Water | 54.3806 |
| Citric Acid | 0.0100 |
| Sorbitol solution | 20.0000 |
| Sodium Saccharin | 0.1170 |
| Hydroxypropyl methylcellulose | 1.0000 |
| Silica | 5.0000 |
| Ethyl alcohol | 18.3030 |
| Polaxamer 407 | 0.2500 |
| Menthol | 0.0323 |
| Thymol | 0.0639 |
| Methyl salicylate | 0.0660 |
| Eucalyptol | 0.0922 |
| Mint Flavor | 0.0850 |
| Sodium Lauryl Sulfate | 0.6000 |
| TOTAL | 100.0000 |

The liquid gel dentifrices of Table 6 were prepared according to the following steps. In Step A, the sodium lauryl sulfate and deionized water were mixed in a first beaker until all solids were dissolved.

In Step B, deionized water was added to a second beaker. Using a Silverson L4RT high shear mixer (Silverson Machines Inc. East Longmeadow, Mass.), the hydroxypropyl methylcellulose was dispersed in the water by sprinkling them in slowly, and mixing until homogeneous. Sorbitol and sodium saccharin were added, and the solution was mixed well until homogeneous. Then, the silica was added the second beaker and mixed until the batch was homogeneous.

In Step C (the alcohol phase), in a third beaker, ethanol, mint flavor, thymol, menthol, methyl salicylate, eucalyptol, and Poloxamer 407 were combined, and mixed until homogeneous.

In the final step, the contents of the third beaker (from Step C) were added to the second beaker (of Step B) and mixed well until homogenous. Finally, the contents of the first beaker (of Step A) were added to the main beaker and mixed until the batch was homogenous.

TABLE 7

Liquid Gel Dentifrices

| Ingredient | 7-1 w/w % | 7-2 w/w % | 7-3 w/w % |
|---|---|---|---|
| Deionized Water | 6218 | 62.23 | 62.5157 |
| Sorbitol (70% Solution) | 20.0000 | 20.0000 | 20.0000 |
| High acyl gellan gum | 0.1000 | 0.1000 | 0.0500 |
| Carrageenan | 0.05 | — | — |
| Hydroxypropyl methylcellulose K100M | — | — | 0.0500 |
| Microcrystalline cellulose | — | — | 1.0000 |
| Ethyl alcohol (200 proof) | 10.000 | 10.0000 | 10.0000 |
| 35% Hydrogen Peroxide solution | — | — | 5.7143 |
| Hydrated silica | 5.0000 | 5.0000 | 5.0000 |
| Sodium lauryl sarcosinate | 0.8000 | 0.8000 | 0.4000 |
| Lauyrl Glucoside | 0.8000 | 0.8000 | 0.4000 |
| Cocamidopropyl betaine | 0.4000 | 0.4000 | 0.2000 |
| Sucralose Solution | 0.1200 | 0.1200 | 0.1200 |
| Sodium Saccharin | 0.1000 | 0.1000 | 0.1000 |
| Flavor - Mint | 0.4500 | 0.4500 | 0.4500 |
| TOTAL | 100.0000 | 100.0000 | 100.0000 |

The liquid gel dentifrices of Table 7 were prepared according to the following steps. In Step A, sodium lauroyl sarcosinate, cocamidopropyl betaine, and deionized water were mixed in a first beaker until all solids were dissolved.

In Step B, deionized water was added to a second beaker. Using a Silverson L4RT high shear mixer (Silverson Machines Inc. East Longmeadow, Mass.), the gellan/carrageenan/celluloses were sprinkled in, and the Silverson L4RT high shear mixer continued to operate until the mixture was homogeneous. The mixer was switched to Caframo mixer (Caframo Limited Wiarton, Ontario, Canada) and mixing continued. Sorbitol, sodium saccharin, and sucralose were added, and the solution was mixed well until homogeneous. The lauryl glucoside was melted, and added to the batch, and mixing was continued until homogeneous. Then, the silica was added and mixed until the batch was homogeneous.

In Step C (the alcohol phase), in a third beaker, ethanol and mint flavor were combined, and mixed until homogeneous.

In the final step, the contents of the third beaker (from Step C) were added to the second beaker (of Step B) and mixed well until homogenous. Finally, the contents of the first beaker (of Step A) and the hydrogen peroxide solution (Formulation 7-3) were added to the main beaker and mixed until the batch was homogeneous.

TABLE 8

Inventive Liquid Gel Dentifrices

| Ingredient | 8-1 w/w % | 8-2 w/w % | 8-3 w/w % | 8.4 w/w % | 8.5 w/w % | 8.6 w/w % |
|---|---|---|---|---|---|---|
| Deionized Water | 57.3044 | 63.0187 | 63.1300 | 58.1687 | 58.8237 | 58.8237 |
| Sorbitol (70% Solution) | 20.0000 | 20.0000 | 20.0000 | 20.0000 | 20.0000 | 20.0000 |
| High acyl gellan gum | 0.1500 | 0.1500 | 0.1500 | — | — | — |
| Iota Carrageenan | — | — | 0.0500 | — | — | — |
| 35% Hydrogen Peroxide solution | 5.7143 | — | — | — | — | — |
| Ethyl alcohol (200 proof) | 10.000 | 10.0000 | 10.0000 | 10.0000 | 10.0000 | 10.0000 |
| Hydrated silica | 5.0000 | 5.0000 | 5.0000 | — | — | — |
| Sodium lauryl sarcosinate | 0.4000 | 0.4000 | 0.4000 | 0.4000 | — | — |
| Lauryl Glucoside | 0.4000 | 0.4000 | 0.4000 | 0.4000 | — | 0.2750 |
| Cocamidopropyl betaine | 0.2000 | 0.2000 | 0.2000 | 0.2000 | — | 0.7400 |
| Sodium trideceth sulfate | — | — | — | — | 1.3300 | — |
| PEG-80 sorbitan laurate | — | — | — | — | 0.2750 | — |
| Sodium lauroamphoacetate | — | — | — | — | 0.7400 | — |
| Sodium methyl cocoyl taurate | — | — | — | — | — | 1.3300 |
| Sodium Fluoride | 0.1613 | 0.1613 | 0.1613 | 0.1613 | 0.1613 | 0.1613 |
| Sucralose Solution | 0.1200 | 0.1200 | 0.1200 | 0.1200 | 0.1200 | 0.1200 |
| Sodium Saccharin | 0.1000 | 0.1000 | 0.1000 | 0.1000 | 0.1000 | 0.1000 |
| Flavor | 0.4500 | 0.4500 | 0.4500 | 0.4500 | 0.4500 | 0.4500 |
| TOTAL | 100.0000 | 100.0000 | 100.0000 | 100.0000 | 100.0000 | 100.0000 |

The inventive liquid gel dentifrices of Table 8 were prepared according to the following steps. In Step A, the surfactant or surfactant combinations (using the sodium lauryl sarcosinate, cocamidopropyl betaine, sodium trideceth sulfate, PEG-80 sorbitan laurate, and/or sodium methyl cocoyl taurate as listed in Table 8), sodium fluoride, and deionized water were mixed in a first beaker until all solids were dissolved.

In Step B, deionized water was added to a second beaker. Using a Silverson L4RT high shear mixer (Silverson Machines Inc. East Longmeadow, Mass.), the gellan and/or carrageenan (if required by the formulation in Table 8) were sprinkled in, and the Silverson L4RT high shear mixer continued to operate until the mixture was homogeneous. The mixer was switched to Caframo mixer (Caframo Limited Wiarton, Ontario, Canada) and mixing continued. Sorbitol, sodium saccharin, and sucralose were added, and the solution was mixed well until homogeneous. The lauryl glucoside (if required by the formulation in Table 8) was melted, and added to the batch, and mixing was continued until homogeneous. Then, the silica (if required by the formulation in Table 8) was added and mixed until the batch was homogeneous.

In Step C (the alcohol phase), in a third beaker, ethanol and mint flavor were combined, and mixed until homogeneous.

In the final step, the contents of the third beaker (from Step C) were added to the second beaker (of Step B) and mixed well until homogenous. Finally, the contents of the first beaker (of Step A) and the hydrogen peroxide solution (as in the case of Formulation 8-1) were added to the main beaker and mixed until the batch was homogeneous.

TABLE 9

Comparative Liquid Gel Dentifrices

| | Formulation | | |
| --- | --- | --- | --- |
| Ingredient | 9-1 w/w % | 9-2 w/w % | 9-3 w/w % |
| Deionized Water | 58.5687 | 53.4187 | 53.3687 |
| Sorbitol (70% Solution) | 20.0000 | 20.0000 | 20.0000 |
| High acyl gellan gum | — | 0.15 | 0.15 |
| Iota Carrageenan | — | — | 0.05 |
| Ethyl alcohol (200 proof) | 10.0000 | 10.0000 | 10.0000 |
| Hydrated silica | — | 5.000 | 5.000 |
| Sodium lauryl sulfate | 0.6000 | 0.6000 | 0.6000 |
| Sodium Fluoride | 0.1613 | 0.1613 | 0.1613 |
| Sucralose Solution | 0.1200 | 0.1200 | 0.1200 |
| Sodium Saccharin | 0.1000 | 0.1000 | 0.1000 |
| Flavor | 0.4500 | 0.4500 | 0.4500 |
| TOTAL | 100.0000 | 100.0000 | 100.0000 |

The comparative liquid gel dentifrices of Table 9 were prepared according to the following steps. In Step A, the sodium lauryl sulfate, sodium fluoride, and deionized water were mixed in a first beaker until all solids were dissolved.

In Step B, deionized water was added to a second beaker. Using a Silverson L4RT high shear mixer (Silverson Machines Inc. East Longmeadow, Mass.), the gellan and/or carrageenan (if required by the formulation in Table 9) were sprinkled in, and the Silverson L4RT high shear mixer continued to operate until the mixture was homogeneous. The mixer was switched to Caframo mixer (Caframo Limited Wiarton, Ontario, Canada) and mixing continued. Sorbitol, sodium saccharin, and sucralose were added, and the solution was mixed well until homogeneous. Then, the silica (if required by the formulation in Table 9) was added and mixed until the batch was homogeneous.

In Step C (the alcohol phase), in a third beaker, ethanol and mint flavor were combined, and mixed until homogeneous.

In the final step, the contents of the third beaker (from Step C) were added to the second beaker (of Step B) and mixed well until homogenous. Finally, the contents of the first beaker (of Step A) was added to the main beaker and mixed until the batch was homogeneous.

The list of ingredients, and their trade names and sources, are shown on Table 10.

TABLE 10

Ingredients list.

| Ingredient | Trade Name | Source |
| --- | --- | --- |
| Acrylate copolymer | Aqua SF-1 (30%) | Lubrizol Corp. |
| Carrageenan | Genuvisco TPC-1 | CP Kelco |
| Citric acid | Citric acid anhydrous | DSM Nutritional Products Inc |
| Cocamidopropyl betaine | Tegobetaine CKD | Degussa |
| Deionized Water | NA | In-house |
| Disodium EDTA | Disodium EDTA | Cognis Corporation |
| Dye | FD&C Green #3 | Sensient Colors |
| Ethyl alcohol | Alcohol USP 195 proof | Pharmco Products |
| Ethyl alcohol | Alcohol USP 200 proof | Pharmco Products |
| Ethyl alcohol | Alcohol USP 195 proof | Pharmco Products |
| Eucalyptol | Eucalyptol | Ungerer and Company |
| Flavor - Mint | N&A SNO Mint 11397 | Firmenich |
| Flavor - Mint | N&A Wintergreen Mint 539274T | Firmenich |
| Flavor - Peppermint | N&A Peppermint Tingle 539314T | Firmenich |
| Glycerin | Glycerin | Cognis Corporation |
| High acyl gellan gum | Kelcogel CG-HA | CP Kelco |
| Hydrated silica | Zeodent 113 | J. M. Huber Corporation |
| Hydrated silica/TiO2 | Sylodent 750 | Grace Davison |
| Hydrogen Peroxide (35% solution) | Peralkali | Degussa |
| Hydroxypropyl methylcellulose K100M | Methocel K100M | Dow Chemical |
| Hydroxypropyl methylcellulose | Methocel 40-202 PCG | Dow Chemical |
| Lauryl glucoside | Plantaren 1200 N UP | Cognis Corp. |
| Low acyl gellen gum | Kelcogel CG-LA | CP Kelco |
| Menthol | L-Menthol, nat. USP/FCC | Polarome International |
| Methylparaben | Nipagin M | Mallinckrodt Baker Inc. |
| Methyl salicylate | Methyl salicylate NF | Rhodia Inc. |
| Microcrystalline cellulose/carboxy methylcellulose sodium | Avicel CL-611 | FMC Corporation |
| Montmorillonite clay | Gelwhite H | Southern Clay Inc. |
| N-Propanol | N-Propanol | Penta Manufacturing Company |
| Polaxamer 407 | Pluronic F-127 | BASF Corporation |
| Sodium Fluoride | Sodium Fluoride Powder | Mallinckrodt Baker Inc. |
| Sodium lauroyl sarcosinate | Hamposyl L-95 | Chattem Chemicals, Inc. |
| Sodium lauryl sulfate | Emicol LZ N | Huntsman |
| Sodium lauryl sulfate | Stepanol WA | Stepan Company |
| Sodium saccharin | Saccharin Sodium Granular, USP | PMC Specialties Group |
| Sodium saccharin | Syncal GS | PMC Specialties |
| Sorbitol | Sorbitol solution (70%), USP | SPI Polyols, Inc. |
| Sucralose | Sucralose solution (25%) | McNeil |
| Thymol | Thymol | Symrise |
| Xanthan gum | Keltrol CG-T | Monsanto Company |
| Xanthan gum | P TIC pre-hydrated rapid - 3 powder | TIC Gums |

Example 2

Rheology Testing

Formulations described in Example 1 were tested for their rheological properties. The same instrumentation was used for both the oscillatory and steady shear measurements. The instrument used was a strain controlled oscillatory rheometer (model RFSII, TA Instruments, New Castle, Del.). Couette and parallel plate geometries were used in all of the testing.

Steady shear viscosity was measured to probe the time dependence and pseudoplasticity of the samples over a broad range of shear rates from 0.02/s to 100/s. These measurements were intended to cover the range of consumer use at both room temperature and body temperature, such as physical appearance, pourability, and tooth swishing. Measurements were made at 0.02, 0.1, 0.5, 1, 10, 25, 50 and 100 $s^{-1}$ for all samples.

For the dynamic oscillatory measurements, the strain sweeps were completed at a frequency of 10 radians/s to determine the viscoelastic region and the frequencies were done in the linear region or near at a strain of 0.02 at RT. The estimation of stability was based on the strength of the gel network. If there was no relaxation, and tan (delta)<1.0, stability was deemed to be good.

Table 11 shows the results of viscosity and tan delta values for various formulations.

TABLE 11

Viscosity (shear rates 10/s and 100/s) and Tan delta (frequencies 0.1 and 100 radians/s).

| Formulation | Comment | Viscosity at 10/s (cP) | Viscosity at 100/s (cP) | Tan delta at 0.1 rad/s | Tan delta at 100 rad/s |
|---|---|---|---|---|---|
| 1-1 | 0.1% gellan | 672 | 68 | 0.21 | 0.44 |
| 1-2 | 0.05% gellan, 0.03% Keltrol Xanthan | 258 | 44 | 0.38 | 0.49 |
| 1-3 | 0.05% gellan | 242 | 32 | 0.30 | 0.38 |
| 2-1 | 0.3% Keltrol Xanthan | 525 | 102 | 0.69 | 0.02 |
| 2-2 | 0.3% TIC Xanthan | | | 1.05 | 0.34 |
| 3-1 | 1% Avicel 611, 0.1% Keltrol Xanthan | 391 | 86 | 0.60 | 0.44 |
| 3-2 | 0.7% Avicel 611, 0.15% Keltrol Xanthan | 382 | 80 | 0.68 | 0.43 |
| 4-1 | Montmorillonite Clay | 172 | 42 | 0.62 | 0.40 |
| 5-1 | Acrylate Copolymer | 89 | 54 | 4.15 | 0.82 |
| 6-1 | 1% HPMC | | | 26.01 | 1.00 |

The table shows that formulations 1-1, 1-2, 1-3, 2-1, 3-1, 3-2, and 4-1 all met the tan delta criteria of less than 1.0 at frequencies 0.1 to 100 rads$^{-1}$, and additionally meet the viscosity criteria at a shear rate of 10 s$^{-1}$ of less than 700 centipoise, and the viscosity criteria at a shear rate of 100 s$^{-1}$ of less than 150 centipoise. Formulation 4-1 contained clay.

Example 3

Stability Testing

All formulations from Example 1 were checked initially and, if no obvious visible (to the unaided eye) signs of sedimentation had occurred, at 1 month, 2 months, 3 months, with the following parameters measured each time:
1) Appearance
2) taste
3) viscosity
4) sedimentation
5) pH Formulations 1-1, 1-2, 1-3, 2-1, 3-1, 3-2 all had no obvious visible (to the unaided eye) signs of sedimentation at 1 month, 2 months, and 3 months. Formulations 5-1 and 6-1, each having tan delta values greater than 1 at 0.1 rads, showed visible (to the unaided eye) sedimentation.

Example 4

Consumer Trial

Formulations from Example 1, Table 7 were used in a small (30 person) consumer trial to compare foaming characteristics of the formulations. Each participant evaluated the three formulations in randomized order. The instructions were to rinse 15 ml of each formulation for 45 seconds, expectorate, and brush with a toothbrush for 1 minute. The participants were asked to wait a minimum of 3 hours between evaluations.

For each formulation, participants were asked to comment on the "Foam consistency" during the late stage of the rinse step, and the "Amount of foam" during the toothbrush step. The possible comments for "Foam consistency" were "Too thick", "Too thin", or "Just about right". The possible comments for "Amount of foam" were "Too much", "Too little", or "Just about right".

Formulation 7-1 used gellan and carrageenan as suspending agents. Formulation 7-2 used only gellan as a suspending agent. Formulation 7-3 used gellan and hydroxypropyl cellulose as suspending agents, and contained hydrogen peroxide as a gas generator.

During the late stage of the rinse step, formulation 7-2 was found to be superior for "Foam consistency", while formulation 7-1 was found to be superior for the "Amount of foam". During brushing, formulations 7-1 and 7-2 were found to be superior for "Foam consistency", while formulation 7-1 was found to be superior for the "Amount of foam".

Example 5

Foam Characteristics Analysis

The distribution of bubble size was determined for formulations from Example 1, Table 8. The foam generating and analysis method used is the foam generation and screening test described above which was designed to generate and measure the diameter of foam bubbles for various formulations such as liquid dentifrice formulas, body wash preparations, shampoos, facial cleansers and other cosmetic product forms that produce foam or lather.

Equipment List
1. Olympus Optical Microscope, Model BX-51 with Discover Details 5 Image Analysis software
2. Oster 14-speed blender (model number 6855)
3. Artificial saliva
4. Microscope slides
5. Beaker
6. Spatula
7. 0.0.625 mm PET (polyethylene terephthalate) spacer (shim stock material)

Procedure:

A mixture was prepared by adding the appropriate amount of each of the formulations in Example 1, Table 8 to the artificial saliva to achieve 80% of formulation in the mixture, the artificial saliva having the following constituents:

| | |
|---|---|
| Sodium Chloride | 1.2236 gm |
| Potassium Chloride | 1.215 gm |
| Calcium Chloride | 0.3178 gm |
| Potassium Phosphate Monobasic | 2.7532 gm |
| Potassium Phosphate Dibasic | 3.5053 gm |
| Deionized Water | 2000 ml |

The mixture was mixed until uniform.

The mixture was placed into the Oster 14-speed (model #6855) Blender and blended for 10 seconds at a speed setting of one (1). A 0.005 gram sample of the foam from the surface of the mixture inside the blender was removed using a spatula.

The 0.005 gram foam sample was placed on a 25 mm×75 mm glass slide having two 0.634 mm PET spacers positioned on each corner of the slide. A second slide was placed onto the first slide and spaced by the PET spacers ensuring that there was a monolayer of foam between the two slides.

The slide was mounted on the Olympus optical microscope (model BX-51 with Discover Details 5 Image Analysis software stage), adjusting the microscope to reflectance mode and capturing the image using the 5× objective and then analyzed. The results are summarized in Table 12.

Formulation 8-1 used gellan as the suspending agent, and contained hydrogen peroxide as a gas generator. Formulation 8-2 used only gellan as the suspending agent. Formulation 8-3 used gellan and carrageenan as the suspending agents.

All foams generated using the inventive formulations comprising surfactant systems of the present invention had a bubble size distribution such that each 0.005 grams of foam had at least 80 bubbles having a diameter of less than 5 μm. Foams generated using the using the inventive formulations comprising the surfactant systems of the present invention in combination with the foam enhancing agents of the present invention, but without incorporating (or free of) a gas generating agent (or material) had a bubble size distribution such that each 0.005 grams of foam had at least 250 bubbles having a diameter of less than 5 μm. This bubble size distribution was surprising similar to the bubble size distribution of about 300 bubbles having a diameter of less than 5 μm per 0.005 grams of foam exhibited by the hydrogen peroxide (or, gas generating agent) containing formulation 8.1.

Foams generated using the comparative formulations 9-1, 9-2, and 9-3, comprising sodium lauryl sulfate had a bubble size distribution such that each 0.005 grams of foam had at least 25 bubbles having a diameter of less than 5 μm. Foams generated using the using the comparative formulations comprising the surfactant systems of the present invention in combination with the foam enhancing agents of the present invention, but without incorporating (or free of) a gas generating agent (or material) exhibited a bubble size distribution such that each 0.005 grams of foam had at least 100 bubbles having a diameter of less than 5 μm. When occupying a an area of 25 mm×75 mm×1.270 mm, however, the 0.005 gram foam samples of the comparative formulations did not correspondingly provide a bubble size distribution such that at least 90% of the bubbles had a diameter of less than about 50 microns.

TABLE 12

Bubble size distribution per 0.005 gm of foam for each inventive formulation in Table 8.

| | Formulation | | | | | |
|---|---|---|---|---|---|---|
| Size range | 8-1 Number | 8-2 Number | 8-3 Number | 8.4 Number | 8.5 Number | 8.6 Number |
| 0-10 μm | 300 | 100 | 275 | 125 | 75 | 105 |
| 10.01-50 μm | 217 | 50 | 220 | 40 | 20 | 27 |
| 50.01-100 μm | 2 | 2 | 3 | 3 | 2 | 3 |
| 100.01-700 μm | 1 | 1 | 2 | 2 | 1 | 2 |
| 700.01-2100 μm | 0 | 0 | 0 | 0 | 0 | 0 |
| Percentage of bubbles < 50 μm | 99.42% | 98.03% | 99% | 97.05% | 96.94% | 94.89% |

TABLE 13

Bubble size distribution per 0.005 gm of foam for each comparative formulation in Table 9.

| | Formulation | | |
|---|---|---|---|
| Size range | 9-1 Number | 9-2 Number | 9-3 Number |
| 0-10 μm | 2 | 40 | 65 |
| 10.01-50 μm | 23 | 60 | 100 |
| 50.01-100 μm | 35 | 150 | 200 |
| 100.01-700 μm | 5 | 0 | 0 |
| 700.01-2100 μm | 0 | 0 | 0 |
| Percentage of bubbles <50 μm | 38.46% | 40.00% | 45.20% |

Example 6

The oral care compositions of the present invention can also be formed in gel mouth rinses. An example of a gel mouth rinse is provided in Table 14.

TABLE 14

| Gel Mouth rinse | |
|---|---|
| Ingredient | w/w % |
| Deionized Water | 66.6255 |
| Disodium EDTA | 0.3000 |
| Sodium Fluoride | 0.1878 |
| Alcohol | 8.4211 |

TABLE 14-continued

Gel Mouth rinse

| Ingredient | w/w % |
|---|---|
| Avicel CL-611 | 0.7000 |
| Xanthan Gum | 0.1500 |
| Carrageenan | 0.0500 |
| Sorbitol | 20.0000 |
| Sucralose | 0.1200 |
| Sodium Saccharin | 0.1170 |
| Sodium Lauroyl Sarcosinate | 0.8000 |
| Cocamidopropyl Betaine | 0.4000 |
| Lauryl Glucoside | 0.8000 |
| Agar, Vitamin E Actate, Pigment | 0.0500 |
| Poloxamer 407 | 0.2500 |
| Menthol | 0.0840 |
| Thymol | 0.1278 |
| Methyl Salicylate | 0.1320 |
| Eucalyptol | 0.1844 |
| Flavor | 0.5000 |
| Color | 0.0004 |
| Total | 100.0000 |

The gel mouth rinse of Table 14 was prepared according to the following steps. In Step A, the disodium EDTA, sodium fluoride, cocamidopropyl betaine, sodium lauroyl sarcosinate, and deionized water were mixed in a first beaker until all solids were dissolved.

In Step B, xanthan gum, in the form of a powder, was added to deionized water in a second beaker to create a 1% solution. Mixing was performed in a Silverson L4RT high shear mixer (Silverson Machines Inc. East Longmeadow, Mass.) until all solids were dissolved.

In Step C, deionized water was added to a third beaker. Using the Silverson L4RT high shear mixer, the carrageenan was dispersed in the water by sprinkling them in slowly, and mixing until homogeneous. The Avicel CL-611 microcrystalline cellulose/sodium carboxy methylcellulose was sprinkled in, and the Silverson L4RT high shear mixer continued to operate until the mixture was homogeneous. The mixer was switched to Caframo mixer (Caframo Limited Wiarton, Ontario, Canada) and mixing continued. sorbitol, sodium saccharin, and sucralose were added, and the solution was mixed well until homogeneous. The lauryl glucoside was melted, and added to the batch, and mixing was continued until homogeneous. The xanthan gum solution (Step B, second beaker) was added to the batch, and mixing continued until homogenous. Then, the agar, vitamin E actate, pigment was added and mixed until the batch was homogeneous.

In Step D (the alcohol phase), in a fourth beaker, ethanol and mint flavor, or ethanol, mint flavor, thymol, menthol, methyl salicylate, eucalyptol, and Poloxamer 407 were combined, and mixed until homogeneous.

In the final step, the contents of the fourth beaker (from Step D) were added to the third beaker (of Step C) and mixed well until homogenous. Finally, the contents of the first beaker (of Step A) were added to the main beaker and mixed until the batch was homogeneous.

What is claimed is:

1. An oral composition comprising:
    a surfactant system, comprising :
        i. at least one alkyl polyglucoside surfactant;
        ii. at least one anionic surfactant; and
        iii. at least one amphoteric surfactant;
    at least one suspending agent selected from the group consisting of high acyl gellan gum and microcrystalline cellulose; and
    an orally acceptable liquid carrier,
    wherein the composition has a pH of from about 4.0 to 8.0 and contains less than 0.01% of bioavailability affecting compounds selected from the group consisting of chemically unmodified clays, water soluble calcium salts, water soluble magnesium salts, water soluble aluminum salts, carbonate salts and mixtures thereof, and wherein said composition has a first viscosity of less than 2000 centipoise at a shear rate of $10s^{-1}$.

2. The composition of claim 1, wherein foams generated by the composition using a foam generation and screening test have a bubble size distribution such that for each 0.005 grams of foam, at least about 80 bubbles have a diameter of less than about 50 microns.

3. The composition of claim 2, wherein the bubble size distribution is such that at least about 125 bubbles have a diameter of less than about 50 microns.

4. The composition of claim 1, further comprising a foam enhancing agent.

5. The composition of claim 4, wherein the foam enhancing agent is selected from the group consisting of natural seaweed extract, natural seed gum, natural plant exudates, natural plant extracts, natural fiber extracts, biosynthetic gums, gelatins, biosynthetic process starch or cellulosic materials, alginates, carrageenans, guar, locust, tara, arabic gum, ghatti gum, agar gum, pectin, salts thereof, and mixtures thereof.

6. The composition of claim 5, wherein the foam enhancing agent is selected from the group consisting of alginates, carrageenans, salts thereof and mixtures thereof.

7. The composition of claim 5, wherein the foam enhancing agent is carrageenan.

8. The composition of claim 1, wherein the anionic surfactant is selected from the group consisting of sarcosine surfactants; taurates; alkyl sulfates; sodium lauryl sulfoacetate; sodium lauroyl isethionate; sodium laureth carboxylate;
    sodium dodecyl benzenesulfonate and mixtures thereof.

9. The composition of claim 8, wherein the anionic surfactant is a sarcosine surfactant.

10. The composition of claim 1, wherein the amphoteric surfactant is selected from the group consisting of alkylimino-diprorionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof.

11. The composition of claim 1, wherein the amphoteric surfactant is an alkylamidopropyl betaine.

12. The composition of claim 1 wherein the composition further has the following physical properties:
    i. a tan delta of less than about 1 at frequencies 0.1 to 100 $rads^{-1}$; and
    ii. a second viscosity of less than about 1000 centipoise at a shear rate of $100s^{-1}$
    and wherein foams generated by the composition using a foam generation and screening test have a bubble size distribution such that for each 0.005 grams of the foam occupying an area of 25mm×75mm×1.270mm, at least 90% of the bubbles have a diameter of less than 50 microns.

13. The composition of claim 12, further comprising an insoluble particulate.

14. The composition of claim 13, wherein the insoluble particulate is a dentally acceptable abrasive.

15. The composition of claim 1 wherein said surfactant system comprises at least one alkyl polyglucoside surfactant, at least one anionic surfactant selected from the group consisting of sarcosine surfactants; taurates; alkyl sulfates; sodium lauryl sulfoacetate; sodium lauroyl isethionate; sodium laureth carboxylate; sodium dodecyl benzenesulfonate and mixtures thereof; and at least one alkylamidopropyl betaine.

16. The composition of claim 5 wherein said surfactant system comprises at least one alkyl polyglucoside surfactant, at least one anionic surfactant selected from the group consisting of sarcosine surfactants; taurates; alkyl sulfates; sodium lauryl sulfoacetate; sodium lauroyl isethionate; sodium laureth carboxylate; sodium dodecyl benzenesulfonate and mixtures thereof; and at least one alkylamidopropyl betaine.

17. The composition of claim 12 wherein said surfactant system comprises at least one alkyl polyglucoside surfactant, at least one anionic surfactant selected from the group consisting of sarcosine surfactants; taurates; alkyl sulfates; sodium lauryl sulfoacetate; sodium lauroyl isethionate; sodium laureth carboxylate; sodium dodecyl benzenesulfonate and mixtures thereof; and at least one alkylamidopropyl betaine and said composition further comprises a foam enhancing agent selected from the group consisting of natural seaweed extract, natural seed gum, natural plant exudates, natural plant extracts, natural fiber extracts, biosynthetic gums, gelatins, biosynthetic process starch or cellulosic materials, alginates, carrageenans, guar, locust, tara, arabic gum, ghatti gum, agar gum, pectin, salts thereof, and mixtures thereof.

18. The composition of claim 1 wherein said surfactant system is present in an amount of from about 0.2% to about 2.5% by weight of the composition.

19. The composition of claim 15 wherein said surfactant system is present in an amount of from about 0.2% to about 2.5% by weight of the composition.

20. The composition of claim 19 wherein said composition comprises from about 0.05% to about 0.5% by weight of the composition of said suspending agent.

* * * * *